United States Patent
Watanabe et al.

(10) Patent No.: US 8,172,754 B2
(45) Date of Patent: May 8, 2012

(54) ULTRASONOGRAPH

(75) Inventors: Yoshinobu Watanabe, Kanagawa (JP);
Yoshinao Tan-naka, Kanagawa (JP);
Takao Suzuki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 539 days.

(21) Appl. No.: 12/297,335

(22) PCT Filed: Apr. 18, 2006
(Under 37 CFR 1.47)

(86) PCT No.: PCT/JP2006/308138
§ 371 (c)(1),
(2), (4) Date: Jan. 23, 2009

(87) PCT Pub. No.: WO2007/122698
PCT Pub. Date: Nov. 1, 2007

(65) Prior Publication Data
US 2009/0275834 A1  Nov. 5, 2009

(51) Int. Cl.
*A61B 8/13* (2006.01)
(52) U.S. Cl. .................. 600/443; 600/437; 600/438
(58) Field of Classification Search .................. None
See application file for complete search history.

(56) References Cited

U.S. PATENT DOCUMENTS

| | | | |
|---|---|---|---|
| 5,840,028 | A | 11/1998 | Chubachi et al. |
| 6,132,373 | A | 10/2000 | Ito et al. |
| 2004/0260180 | A1* | 12/2004 | Kanai et al. ............. 600/449 |
| 2007/0123777 | A1 | 5/2007 | Watanabe et al. |
| 2009/0024032 | A1 | 1/2009 | Kato et al. |

FOREIGN PATENT DOCUMENTS

| | | |
|---|---|---|
| EP | 1421905 A1 | 5/2004 |
| EP | 1529491 A1 | 5/2005 |
| EP | 1637082 A1 | 3/2006 |
| JP | 10-5226 | 1/1998 |
| JP | 11-318896 | 11/1999 |

(Continued)

OTHER PUBLICATIONS

European Search Report for corresponding application No. 06745420.7 issued Dec. 23, 2009.

(Continued)

*Primary Examiner* — Long V. Le
*Assistant Examiner* — Bradley Impink
(74) *Attorney, Agent, or Firm* — Renner, Otto, Boisselle & Sklar, LLP

(57) ABSTRACT

An ultrasonic diagnostic apparatus according to the present invention includes: a transmitting section for driving an ultrasonic probe to transmit an ultrasonic wave toward a measuring region of a subject, including an arterial vascular wall; a receiving section for receiving a reflected wave, produced by getting the ultrasonic wave reflected from the subject, at the probe, thereby generating a received signal; a displacement detecting section for calculating the magnitude of displacement of each measuring point in the measuring region on the wall by analyzing the received signal; a tissue-to-present determining section, which defines at least one boundary between tissues included in the measuring region on the wall and which selects one of at least two areas divided by the boundary defined; and a property value calculating section for calculating a property value of the subject based on the magnitude of displacement of each measuring point. The distribution of property values of the measuring points in the area selected by the tissue-to-present determining section is presented as a two-dimensional image.

17 Claims, 9 Drawing Sheets

FOREIGN PATENT DOCUMENTS

| | | |
|---|---|---|
| JP | 2000-229078 | 8/2000 |
| JP | 2000-271117 | 10/2000 |
| WO | 01/47421 A1 | 7/2001 |
| WO | 2004/112568 | 12/2004 |
| WO | 2006/043529 A1 | 4/2006 |

OTHER PUBLICATIONS

International Search Report for corresponding Application No. PCT/JP2006/308138 mailed Oct. 10, 2006.

Hiroshi Kanai et al., "Imaging of Elasticity Distribution in Arterial Wall by Transcutaneous Ultrasound and Electronic Staining" The Japanese Journal of Clinical Pathology, 2003, vol. 51, No. 8, pp. 805-812.

B.H. Ong et al., "Clinical Demonstration of Functional Wave Front of the Intramyocardial Ischemic Region in Patients with Coronary Stenosis" 2003 IEEE Ultrasonics Symposium Proceedings, pp. 1843-1846.

Form PCT/ISA/237 and a partial English translation for Application No. PCT/JP2006/308138.

* cited by examiner

ULTRASONOGRAPH

TECHNICAL FIELD

The present invention relates to an ultrasonic diagnostic apparatus and more particularly relates to an ultrasonic diagnostic apparatus that can obtain an attribute value of a blood vessel.

BACKGROUND ART

An ultrasonic diagnostic apparatus is used to make a non-invasive checkup on a subject by irradiating him or her with an ultrasonic wave and analyzing the information contained in its reflected wave (i.e., echo). For example, a conventional ultrasonic diagnostic apparatus that has been used extensively converts the intensity of the reflected wave into its associated pixel luminance, thereby presenting the subject's structure as a tomographic image. In this manner, the internal structure of the subject can be known.

Meanwhile, some people are attempting recently to track the motion of a subject's tissue more precisely and evaluate the strain and the elasticity, viscosity or any other physical (attribute) property of the tissue (among other things, an arterial vascular wall) mainly by analyzing the phase of the reflected wave (Patent Document No. 1 or 2).

If the elastic property of each site of the arterial vascular wall under inspection is presented as a two-dimensional distribution by using such a technique, a portion of the arterial vascular wall with a unique elastic modulus can be easily identified. That is why an ultrasonic diagnostic apparatus could be used in diagnosing arterial sclerosis.

Patent Document No. 1: Japanese Patent Application Laid-Open Publication No. 10-5226

Patent Document No. 2: Japanese Patent Application Laid-Open Publication No. 2000-229078

Patent Document No. 3: Pamphlet of PCT International Application Publication No. 2004/112568

Patent Document No. 4: Japanese Patent Application Laid-Open Publication No. 2000-271117

DISCLOSURE OF INVENTION

Problems to be Solved by the Invention

In presenting an attribute property value representing an elastic property, for example, as a two-dimensional distribution image, only the attribute property values at respective sites of the subject are displayed as pieces of information without reflecting any structural difference of the subject. For example, if the adventitia and its adjacent media of an arterial vascular wall have the same tissue hardness, then their elastic moduli will also be the same, thus making no difference in the information displayed.

However, in order to make a more accurate pathological diagnosis on the subject, it would be more beneficial to allow the person making the diagnosis to determine what tissue the region of interest belongs to.

In order to overcome the problems described above, the present invention has an object of providing an ultrasonic diagnostic apparatus that can selectively present the elastic modulus distribution of any arbitrary tissue in the subject.

Means for Solving the Problems

An ultrasonic diagnostic apparatus according to the present invention includes: a transmitting section for driving an ultrasonic probe that sends out an ultrasonic wave toward a measuring region of a subject, the region including an arterial vascular wall; a receiving section for receiving a reflected wave, produced by getting the ultrasonic wave reflected from the subject, at the ultrasonic probe, thereby generating a received signal; a displacement detecting section for calculating the magnitude of displacement of each measuring point in the measuring region on the vascular wall by analyzing the received signal; a tissue-to-present determining section, which defines at least one boundary between multiple tissues included in the measuring region on the vascular wall and which selects one of at least two areas that have been divided by the boundary defined; and a property value calculating section for calculating a property value of the subject based on the magnitude of displacement of each said measuring point. The distribution of property values of the measuring points included in the area that has been selected by the tissue-to-present determining section is presented as a two-dimensional image.

In one preferred embodiment, the tissue-to-present determining section includes: a boundary defining section for defining at least one boundary between the multiple tissues included in the vascular wall; and an area selecting section for selecting one of at least two areas that have been divided by the boundary defined. The area selecting section generates the location information of the one area in accordance with an operator's command.

In this particular preferred embodiment, the ultrasonic diagnostic apparatus further includes: an image processing section for generating a tomographic image of the measuring region of the subject based on the received signal; and a display section for presenting the tomographic image.

In a specific preferred embodiment, the boundary defining section generates the location information of the at least one boundary based on a location that has been specified by the operator on the tomographic image presented on the display section.

In another preferred embodiment, the boundary defining section automatically generates the location information of the at least one boundary based on the received signal.

In this particular preferred embodiment, the ultrasonic diagnostic apparatus further includes a storage section that stores not only the location information of the at least one boundary but also information about the tomographic image and information about the magnitudes of displacement of the respective measuring points in association with points in time when, or the order in which, the received signals arrived.

In a specific preferred embodiment, the ultrasonic diagnostic apparatus reads the information about the tomographic image from the storage section to present the tomographic image on the display section. The boundary defining section reads the location information of the at least one boundary between the tissues from the storage section. And the boundary defining section updates the location of the at least one boundary based on the location that has been specified by the operator on the tomographic image presented on the display section.

In another preferred embodiment, the boundary defining section automatically generates the location information of the at least one boundary based on the received signal, and updates the location information of the at least one boundary generated based on the location that has been specified by the operator on the tomographic image presented on the display section.

In still another preferred embodiment, the property value is an elastic modulus.

In yet another preferred embodiment, the ultrasonic diagnostic apparatus further includes a region-of-interest designating section for allowing the operator to designate a region of interest within the measuring region based on the tomographic image presented on the display section. The property value calculating section calculates a property value of the subject based on the magnitude of displacement of a measuring point inside the region of interest.

In this particular preferred embodiment, the property value calculating section further calculates at least one of the average, maximum value, minimum value and variance of elastic moduli within the region of interest.

In an alternative preferred embodiment, the property value calculating section further figures out the distribution of elastic moduli within the region of interest and presents the distribution of elastic moduli as a histogram on the display section.

In yet another preferred embodiment, the vascular wall includes an intima, a media and an adventitia and the at least one boundary is at least one of a boundary between the intima and a vascular lumen, a boundary between the intima and the adventitia, and a boundary between the adventitia and an extravascular tissue.

A control method according to the present invention is a method for controlling an ultrasonic diagnostic apparatus using a control section of the apparatus. The method includes the steps of: (A) driving an ultrasonic probe and sending out an ultrasonic wave; (B) receiving a reflected wave from a subject, including an arterial vascular wall, at the ultrasonic probe, thereby generating a received signal; (C) calculating the magnitude of displacement of each measuring point in a measuring region on the vascular wall by analyzing the received signal; (D) defining at least one boundary between multiple tissues included in the measuring region on the vascular wall and selecting one of at least two areas that have been divided by the boundary defined; (E) calculating a property value of the subject based on the magnitude of displacement of each said measuring point; and (F) presenting the property values of the measuring points included in the at least one area as a two-dimensional image.

In one preferred embodiment, the step (D) includes the steps of: (D1) defining at least one boundary between the multiple tissues included in the vascular wall; and (D2) selecting one of the at least two areas that have been divided by the boundary defined. The step (D2) includes generating the location information of the one area in accordance with an operator's command.

In this particular preferred embodiment, the method further includes the steps of: (G) generating a tomographic image of the measuring region of the subject based on the received signal; and (H) presenting the tomographic image.

In another preferred embodiment, the step (D1) includes generating the location information of the at least one boundary based on a location that has been specified by the operator on the tomographic image.

In still another preferred embodiment, the step (D1) includes automatically generating the location information of the at least one boundary based on the received signal.

In this particular preferred embodiment, the method further includes, between the steps (D) and (E), the step (I) of storing, in the storage section, not only the location information of the at least one boundary but also information about the tomographic image and information about the magnitudes of displacement of the respective measuring points in association with points in time when, or the order in which, the received signals arrived.

In a specific preferred embodiment, the method further includes, between the steps (D) and (E), the step (J) of reading the information about the tomographic image from the storage section to present the tomographic image on the display section, and making the boundary defining section retrieve the location information of the at least one boundary between the tissues from the storage section, and the step (K) of updating the location information of the at least one boundary by allowing the operator to modify the location of the at least one boundary on the tomographic image.

EFFECTS OF THE INVENTION

According to the present invention, the boundary between arbitrary tissues on a subject can be detected and a two-dimensional distribution image of elastic moduli can be presented for the tissues specified by the operator. As a result, the distribution of elastic moduli can be known, and the pathological diagnosis of the subject can be made more accurately, on a tissue-by-tissue basis within the measuring region.

DESCRIPTION OF REFERENCE NUMERALS

Figure 1:
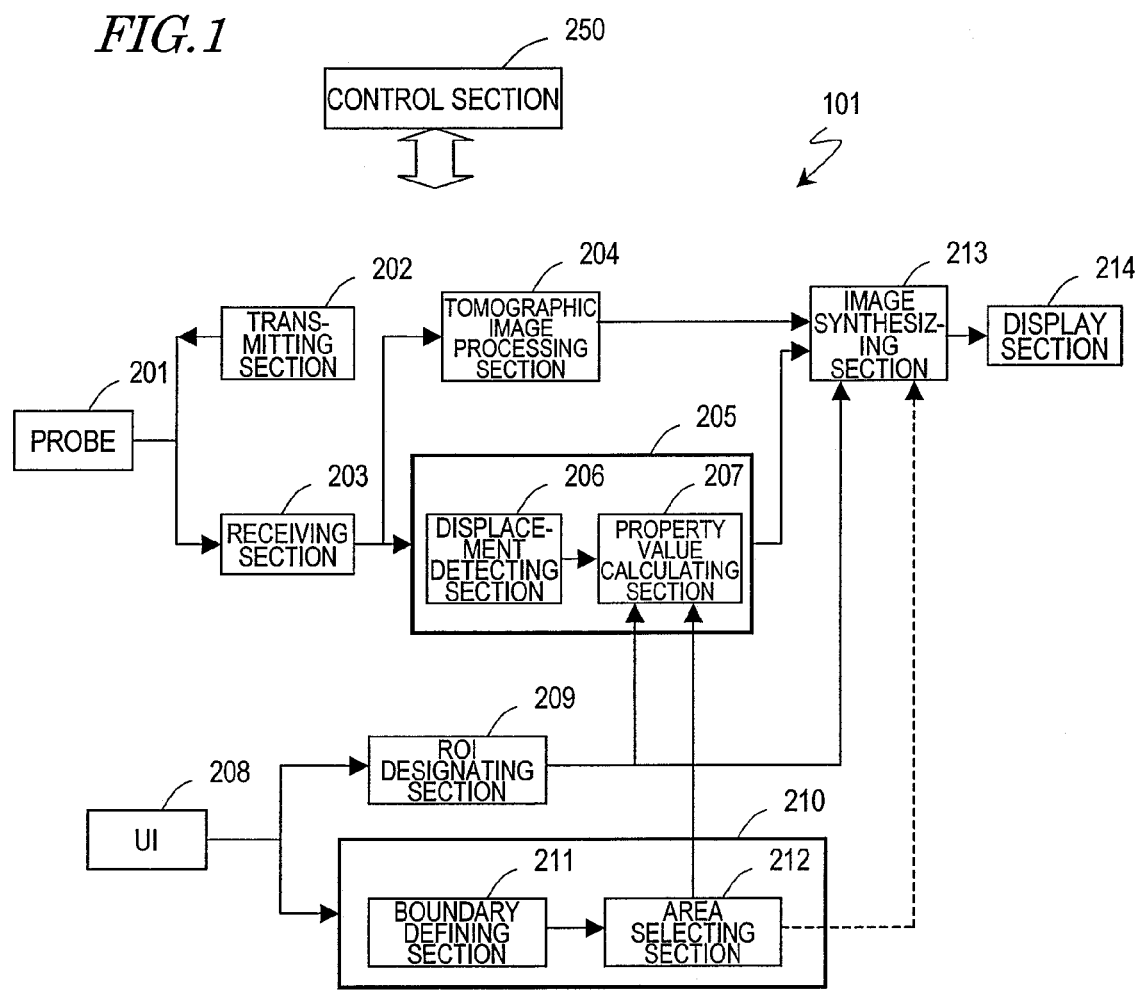
FIG. 1 is a block diagram illustrating a first preferred embodiment of an ultrasonic diagnostic apparatus according to the present invention.

101, 102, 103 ultrasonic diagnostic apparatus
201 probe 202 transmitting section
203 receiving section
204 tomographic image processing section
205 computing section
206 displacement detecting section
207 property value calculating section
208 user interface
209 region-of-interest designating section
210 tissue-to-present determining section
211, 221, 223 boundary defining section
212 area selecting section
213 image synthesizing section
214 display section
250 control section
251 memory

BEST MODE FOR CARRYING OUT THE INVENTION (Embodiment 1)

Hereinafter, a first preferred embodiment of an ultrasonic diagnostic apparatus according to the present invention will be described. The ultrasonic diagnostic apparatus of the present invention is used to measure the elastic modulus, magnitude of strain, coefficient of viscosity or any other attribute property value of a vascular wall. In the following description of preferred embodiments, the ultrasonic diagnostic apparatus is supposed to calculate the elastic modulus as an attribute property value. Alternatively, the apparatus may also calculate the magnitudes of strains or the coefficients of viscosity and present an image representing the two-dimensional distribution thereof.

FIG. 1 is a block diagram showing a configuration for an ultrasonic diagnostic apparatus 101 as a first preferred embodiment of the present invention. The ultrasonic diagnostic apparatus 101 includes a transmitting section 202, a receiving section 203, a tomographic image processing section 204, a computing section 205, a region-of-interest designating section 209, a tissue-to-present decision section 210 and an image synthesizing section 213. The apparatus further includes a control section 250 for controlling all of these elements and a user interface 208. The control section 250 may be implemented as a microcomputer, for example. The user interface 208 is an input device such as a keyboard, a mouse, a track ball, a switch, or a button that accepts an operator's input.

The ultrasonic diagnostic apparatus 101 is connected to a probe 201, which sends out an ultrasonic wave toward a measuring region of a subject and receives a reflected wave, produced by getting the ultrasonic wave reflected from the subject.

In accordance with the instruction given by the control section 250, the transmitting section 202 generates a high-voltage transmission signal that drives the probe 201 at a specified timing. The probe 201 converts the transmission signal that has been generated by the transmitting section 202 into an ultrasonic wave and sends out the ultrasonic wave toward a subject, and also converts a reflected wave that has been reflected by an internal organ of the subject into an electrical signal. A number of piezoelectric transducers are arranged in the probe 201. By changing the piezoelectric transducers to use or the timing to apply a voltage to the piezoelectric transducers, the probe 201 controls the angle of deflection and focus of the ultrasonic waves to transmit and receive. The receiving section 203 amplifies the electrical signal that has been generated by the probe 201, and outputs a received signal. In this manner, the receiving section 203 detects either only an ultrasonic wave that has been reflected from a predetermined point (i.e., a focused ultrasonic beam) or only an ultrasonic wave that has come from a predetermined direction (or at a predetermined angle of deflection). The ultrasonic waves are usually transmitted and received a number of times (e.g., ten plus times) a second.

The tomographic image processing section 204 includes a filter, a detector, and a logarithmic amplifier, and analyzes mainly the amplitude of the received signal, thereby sequentially generating image signals representing tomographic images of the subject. Those signals generated are output to the image synthesizing section 213.

The image synthesizing section 213 synthesizes together the tomographic image represented by the image signal and the image representing the two-dimensional distribution of attribute property values that have been calculated by the property value calculating section 207, and outputs the synthetic image thus obtained to the display section 214.

The region-of-interest designating section 209 generates the location information of a target region within the measuring region, which has been designated by the operator on the tomographic image on the display section 214 with the user interface 208. That region designated by the operator is a target region where the attribute property value needs to be calculated, and is called a "region-of-interest". The location information of the region-of-interest thus generated is output to the image synthesizing section 213 and the property value calculating section 207.

The tissue-to-present determining section 210 determines the location information of the target tissue for the operator where the attribute property needs to be calculated. For that purpose, the tissue-to-present determining section 210 includes a boundary defining section 211 and an area selecting section 212. The boundary defining section 211 automatically defines the location of at least one boundary between multiple tissues included in the arterial vascular wall of the subject, thereby generating location information. The boundary location information thus generated is output to the image synthesizing section 213 so that the boundary is indicated on the tomographic image on the display section 214.

The arterial vascular wall of the subject includes an intima, a media and an adventitia. Furthermore, outside of the adventitia, there is an extravascular tissue. And the intima is adjacent to the vascular lumen. The boundaries between these tissues can be detected automatically by a known technique (which may be the one disclosed in Patent Document No. 3 or 4). More specifically, the boundaries may be detected based on the magnitude of displacement of the measuring point that has been obtained from the displacement detecting section 206 and the amplitude intensity of the received signal that has been obtained from the tomographic image processing section 204. If the best detection method changes according to the type of the boundary, then the boundaries may be detected by multiple different detection methods. For example, since blood is flowing inside the vascular lumen, the boundary between the vascular lumen and the intima may be detected by analyzing the received signal by the Doppler's method.

The tissue-to-present determining section 210 may detect and select the boundaries either over the entire measuring region or only the region-of-interest that has been defined within the measuring region. However, the amount of computations to be done would be the smaller if the boundaries are detected and selected within the region-of-interest.

Using the user interface 208, the operator selects one of at least two areas that have been defined by at least one boundary being superimposed on the tomographic image. The area selecting section 212 generates the location information of the area that has been selected by the operator. The selected area's location information thus generated is output to the property value calculating section 207 to be described later.

The computing section 205 includes the displacement detecting section 206 and the property value calculating section 207. The displacement detecting section 206 analyzes the received signal, thereby sequentially calculating the magnitudes of displacement of the respective measuring points that have been set within the measuring region of the subject. The method of calculating the magnitudes of displacement is not particularly limited but may be any known method. To calculate the magnitude of displacement with high precision, the phase difference tracking method as disclosed in Patent Document No. 1 may be used, for example. More particularly, the magnitude of displacement of the subject's tissue in the ultrasonic wave transmitting and receiving directions may be figured out by analyzing the phase difference between the received signals.

The property value calculating section 207 calculates an attribute property value such as the magnitude of strain or elastic modulus in accordance with the location information of the region-of-interest that has been provided by the region-of-interest designating section 209 and based on the magnitudes of displacement of the measuring points within the region-of-interest. More specifically, first, the property value calculating section 207 adds the magnitude of displacement that has been calculated by the displacement detecting section 206 to the original location of each measuring point, thereby finding the location of the measuring point displaced and plotting a location change waveform representing the change of locations of each measuring point. By calculating the difference between the location change waveforms of two adjacent measuring points or two arbitrary measuring points within the measuring region, a thickness variation waveform $\Delta W$ is obtained. And by dividing the thickness variation waveform $\Delta W$ by an initial value Ws, the magnitude of strain $\epsilon$ can be obtained.

The property value calculating section 207 is further provided externally with information about the blood pressure of the subject. For example, the subject's blood pressure is measured with a blood pressure manometer and the property value calculating section 207 receives the blood pressure value from the blood pressure manometer. Supposing the difference between the highest and lowest blood pressures is identified by $\Delta P$, the radial elastic modulus Er is calculated by $Er=\Delta P/\epsilon=\Delta P \cdot Ws/\Delta W$. This elastic modulus Er is obtained between every pair of adjacent measuring points within the measuring region. As a result, a two-dimensional distribution of elastic moduli in the measuring region can be obtained. As the highest and lowest blood pressures are normally measured every cardiac cycle, the elastic modulus Er is also measured every cardiac cycle.

The property value calculating section 207 may calculate the attribute property values either only at measuring points within the selected area, representing the tissue that the operator is interested in, or using every measuring point within the region-of-interest.

The property value calculating section 207 further obtains the maximum, minimum, average and variance values of the elastic moduli that have been measured within the selected area. Optionally, the property value calculating section 207 may also obtain the frequency distribution of elastic moduli. These values calculated are output to the image synthesizing section 213.

The image synthesizing section 213 receives the elastic moduli that have been calculated by the property value calculating section 207, thereby generating an image representing the two-dimensional distribution of the elastic moduli. In this case, if the elastic moduli have been obtained only within the selected area, the image synthesizing section 213 generates the two-dimensional distribution image using every elastic modulus received from the property value calculating section 207. On the other hand, if the property value calculating section 207 has obtained elastic moduli within the region-of-interest, then the image synthesizing section 213 receives the location information of the selected area from the tissue-to-present determining section 210 and generates the two-dimensional distribution image only within the selected area.

The two-dimensional distribution image of elastic moduli thus generated is synthesized with the tomographic image of the subject's measuring region, which has been provided by the tomographic image processing section 204. The image synthesizing section 213 also receives the location information of the region-of-interest from the region-of-interest designating section 209 and the location information of the boundary from the tissue-to-present determining section 210, thereby generating line segments representing the region-of-interest and the boundary, respectively, and synthesizing those line segments with the tomographic image.

Furthermore, the image synthesizing section 213 generates numerical values representing the maximum, minimum, average and variance values of the elastic moduli that have been obtained by the property value calculating section 207. If a frequency distribution of the elastic moduli has been obtained, a histogram of the elastic moduli is generated.

On the other hand, if the property value calculating section 207 has not calculated the elastic moduli yet, then line segments representing the region-of-interest and the boundary are generated and synthesized with the tomographic image.

The display section 214 receives and displays the image information that has been generated by the image synthesizing section 213.

It should be noted that the respective elements of the ultrasonic diagnostic apparatus 101 described above could be implemented as hardware components or by a software program. The region designating section 209 and the tissue-to-present determining section 210 may be implemented by a microcomputer including the control section 250.

Figure 2:
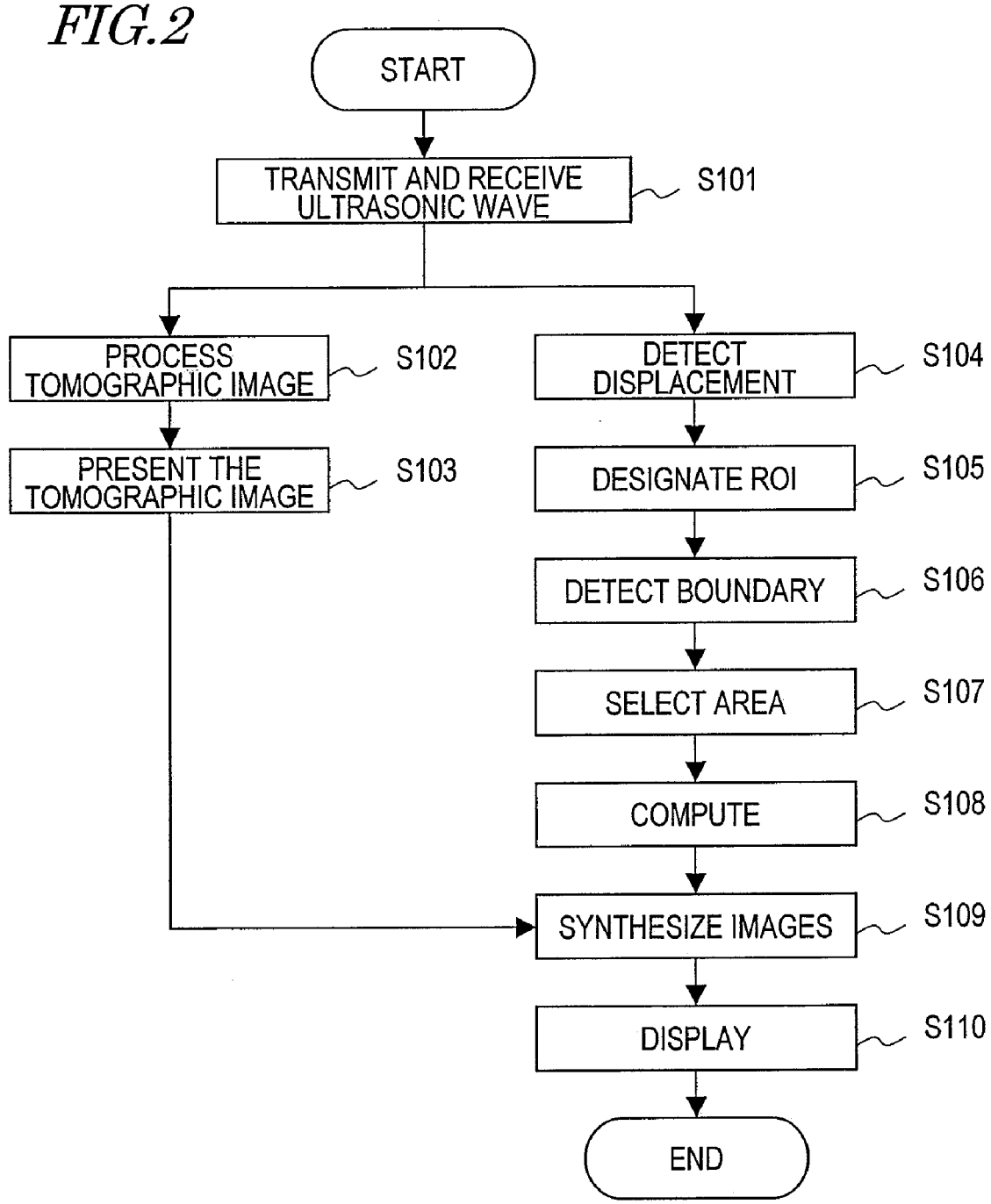
FIG. 2 is a flowchart showing how the ultrasonic diagnostic apparatus shown in FIG. 1 operates.
Figure 3:
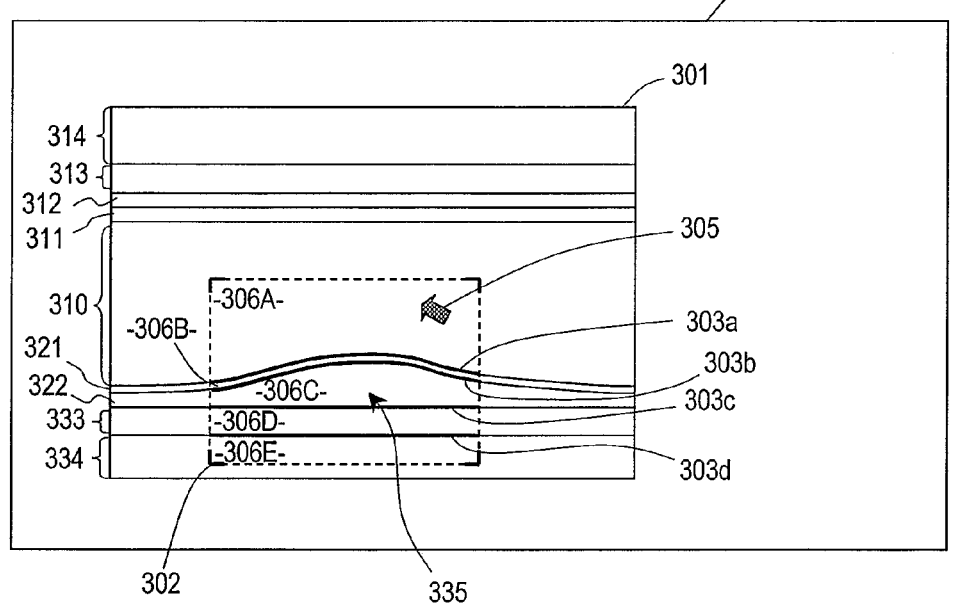
FIG. 3 illustrates an example of an image to be presented on the display section of the ultrasonic diagnostic apparatus shown in FIG. 1.
Figure 4:
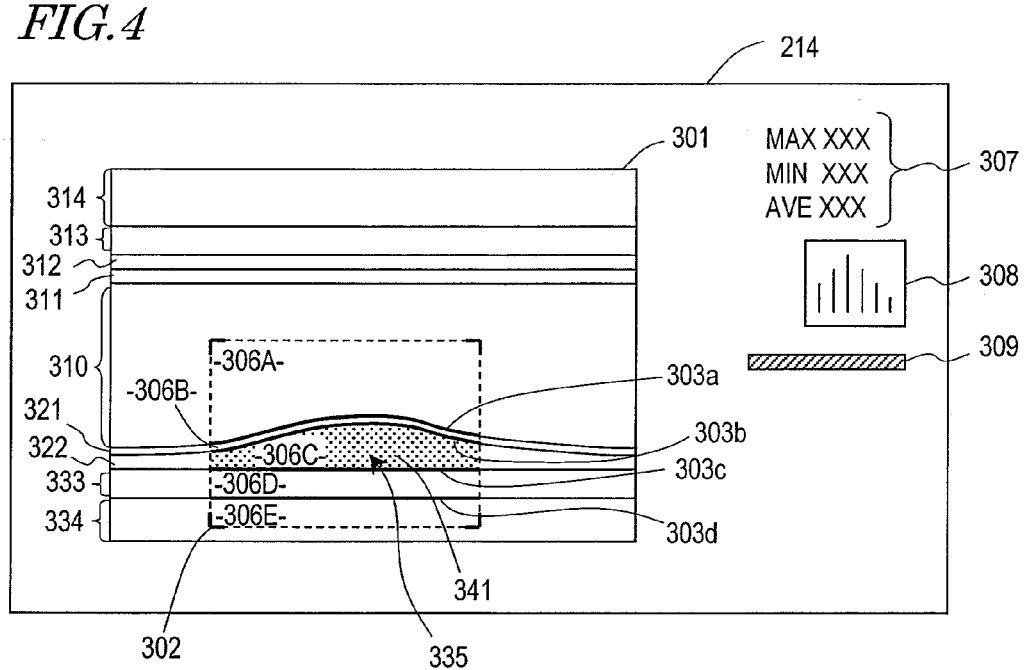
FIG. 4 illustrates another example of an image to be presented on the display section of the ultrasonic diagnostic apparatus shown in FIG. 1.
Figure 5:
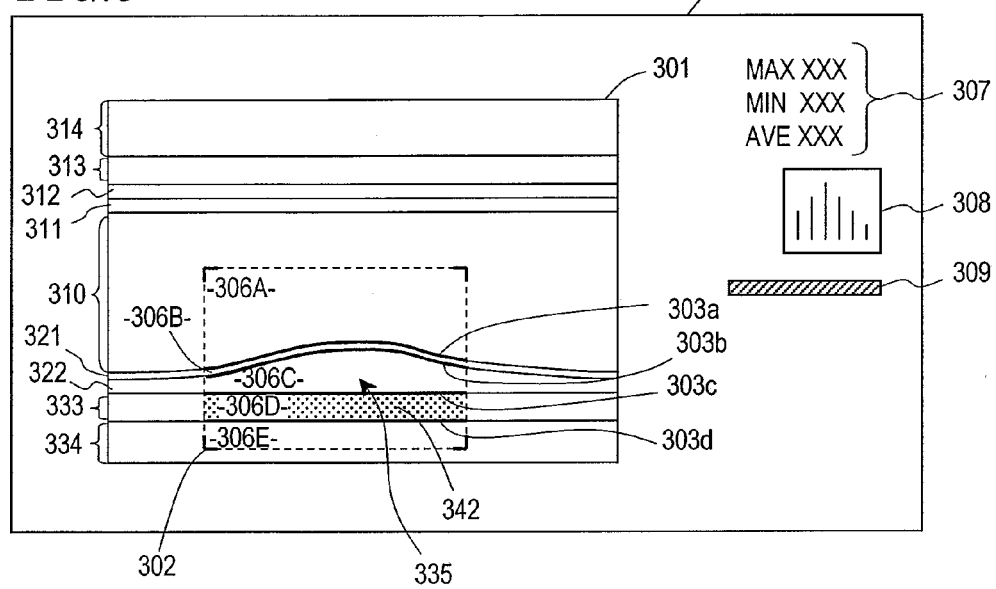
FIG. 5 illustrates still another example of an image to be presented on the display section of the ultrasonic diagnostic apparatus shown in FIG. 1.

Hereinafter, it will be described with reference to FIG. 1 and FIGS. 2 to 5 how the ultrasonic diagnostic apparatus 101 operates. FIG. 2 is a flowchart showing the procedure of operation of the ultrasonic diagnostic apparatus 101. FIGS. 3 to 5 illustrate exemplary images to be presented on the display section 214.

First, the transmitting section 202 drives the probe 201, thereby sending out an ultrasonic wave toward a subject including his or her arterial vascular wall. Then, a reflected wave, produced by getting the ultrasonic wave reflected by the subject, is received at the receiving section 203 through the probe 201, thereby generating a received signal in Step S101.

The tomographic image processing section 204 receives the received signal and transforms the amplitude of the received signal into luminance information, thereby generating an image signal representing a tomographic image (in Step S102). Then, the image signal is output to the display section 214 by way of the image synthesizing section 213, and the tomographic image is presented on the display section (in Step S103).

As shown in FIG. 3, a tomographic image 301 is presented on the screen of the display section 214. The tomographic image 301 includes the intima 311, media 312 and adventitia 313 of a vascular anterior wall, the intima 321, media 322 and adventitia 333 of a vascular posterior wall, a vascular lumen 310, and extravascular tissues 314 and 334. In FIG. 3, the boundaries between these tissues are represented by line segments. In an actual tomographic image, however, these tissues are presented with luminances representing the intensities of the reflected ultrasonic waves. That is why the boundaries between those tissues may sometimes be not so clearly defined.

While the tomographic image is being generated, the displacement detecting section 206 of the computing section 205 analyzes the received signal, thereby calculating the magnitudes of displacements of respective measuring points within the measuring region of the subject (in Step S104).

The operator defines a region-of-interest 302 on the tomographic image 301 presented on the display section 214 using a user interface 208 such as a mouse. In the example illustrated in FIG. 3, the region-of-interest 302 is defined by the operator so as to include an atheroma 335 that is observed on the vascular posterior wall. In accordance with the signal that has been entered through the user interface 208, the ROI designating section 209 determines the location information of the region-of-interest 302 within the measuring region (in Step S105). Optionally, the region-of-interest may also be defined after a target area where an attribute property value needs to be calculated has been selected.

The boundary defining section 211 of the tissue-to-present determining section 210 automatically detects the boundaries between the respective tissues, which are included in the arterial vascular wall, within the region-of-interest 302 based on the received signal. The location information of the boundaries detected is passed to the image synthesizing section 213 and then displayed on the display section 214. As shown in FIG. 3, within the region-of-interest 302, the boundary 303a between the vascular lumen 310 and the intima 321, the boundary 303b between the intima 321 and the media 322, the boundary 303c between the media 322 and the adventitia 333, and the boundary 303d between the adventitia 333 and the extravascular tissue 334 are superimposed on the tomographic image 301.

Then, the operator chooses one of the areas 306A, 306B, 306C, 306D and 306E, which have been defined by these boundaries 303a through 303d, as a target area where the attribute property value needs to be calculated. By moving the cursor 305 with the user interface 208 as shown in FIG. 3, for example, the operator designates one particular area. In accordance with the signal supplied from the user interface 208, the area selecting section 212 generates the location information of the selected area that has been designated by the operator and outputs the information to the property value calculating section 207 and the image synthesizing section 213 (in Step S107).

Based on the magnitudes of displacement at the respective measuring points that have been provided by the displacement detecting section 206 and the location information of the selected area that has been provided by the tissue-to-present determining section 210, the property value calculating section 207 calculates the elastic modulus between the measuring points within the selected area. The property value calculating section 207 also obtains the maximum, minimum and average values and frequency distribution of the elastic moduli within the selected area (in Step S108).

The image synthesizing section 213 generates a two-dimensional distribution image based on the elastic moduli that have been calculated by the property value calculating section 207 and synthesizes the distribution image and the tomographic image together (in Step S109). The image synthesizing section 213 also generates numerical values representing the maximum, minimum and average values and further generates a histogram of the elastic moduli. The image thus generated is presented on the display section 214 (in Step S110).

After that, either the region-of-interest or the selected area where the attribute property value needs to be obtained may be modified or changed if necessary. In that case, the same series of processing steps that starts with Step S105 should be carried out all over again.

In FIG. 3, if the operator has selected the area 306C interposed between the boundaries 303b and 303c, then a two-dimensional distribution image 341 of elastic moduli within the area 306C is superimposed on the tomographic image 301 as shown in FIG. 4. The area 306C is portion of the designated region-of-interest 302 that represents the media of the vascular posterior wall. In FIG. 4, the two-dimensional distribution image 335 is indicated by even shadowing. Actually, however, the two-dimensional distribution image 335 is presented in color tones or grayscale tones associated with the elastic moduli, and a color bar 309 or a grayscale bar 309 representing the correspondence between the elastic moduli and the color tones or grayscale tones is also displayed. Maximum, minimum and average values 307 of elastic moduli in the selected area 306C and histograms 308 of the elastic moduli are also displayed. The measuring points are set in the entire region-of-interest 302 such that the distribution of elastic moduli can be presented as a two-dimensional matrix consisting of 64 vertical pixels by 32 horizontal pixels, for example.

On the other hand, if the operator has selected the area 306D interposed between the boundaries 303c and 303d in FIG. 3, then a two-dimensional distribution image 342 of elastic moduli within the area 306D is superimposed on the tomographic image 301 as shown in FIG. 5. The area 306D is a portion of the designated region-of-interest 302 that represents the adventitia of the vascular posterior wall.

By displaying the distributions of elastic moduli on a tissue-by-tissue basis as shown in FIGS. 4 and 5, it becomes clearer what tissue a portion with a specific elastic modulus belongs to. As a result, a person who is carrying out the diagnosis (such as a doctor) can estimate the elastic moduli with the tissue-by-tissue properties into consideration. Thus, according to this preferred embodiment, a boundary between tissues in a subject can be located automatically, and an image representing the two-dimensional distribution of elastic moduli can be presented for a tissue specified by the operator. Consequently, the distribution of elastic moduli can be known for every tissue within the measuring region, and a more accurate pathological diagnosis can be made on the given subject.

In the preferred embodiment described above, the boundary defining section 211 locates the boundaries between the respective tissues that form the vascular wall. However, a plurality of tissues may be detected collectively. For example, the intima and the media may be detected as an intima-media thickness (IMT) and the boundary between the IMT and the adventitia and the boundary between the IMT and the vascular lumen may be located.

(Embodiment 2)

Figure 6:
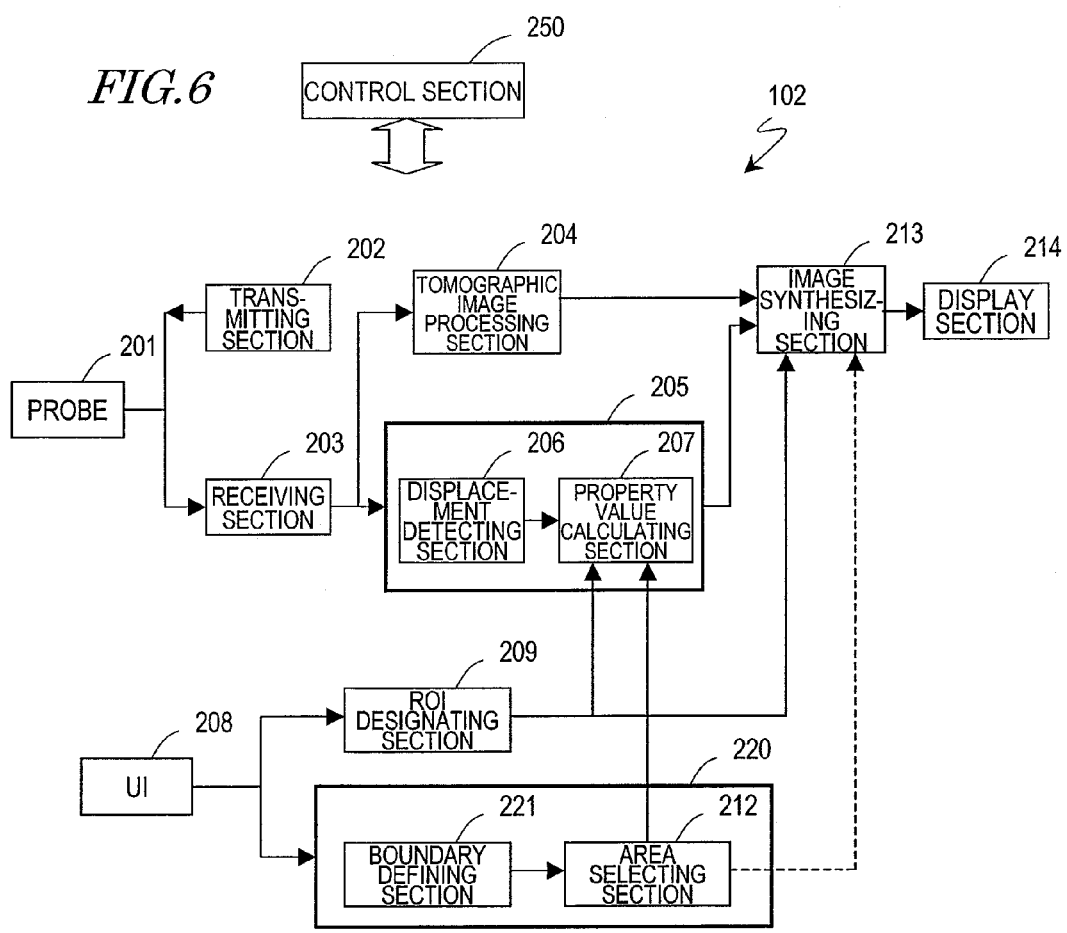
FIG. 6 is a block diagram illustrating a second preferred embodiment of an ultrasonic diagnostic apparatus according to the present invention.

Hereinafter, a second preferred embodiment of an ultrasonic diagnostic apparatus according to the present invention will be described. FIG. 6 is a block diagram showing a configuration for an ultrasonic diagnostic apparatus 102 as a second preferred embodiment of the present invention. Unlike the first preferred embodiment, the ultrasonic diagnostic apparatus 102 includes a tissue-to-present determining section 220 including the boundary defining section 221.

The boundary defining section 221 defines the at least one boundary by the location that has been specified by the operator on the tomographic image 301 being presented on the display section 214, and generates its location information. More specifically, using the user interface 208, the operator moves the cursor on the tomographic image 301 being presented on the display section 214. The trace of the cursor on the move is superimposed as a line segment on the tomographic image 301. If the operator finds the line segment drawn appropriately, then he or she determines his or her selection with the user interface 208, thereby fixing the boundary that has been specified by him or her. If necessary, one or more line segments may be drawn and fixed as additional boundaries. The boundary defining section 221 generates the location information of the boundaries that have been fixed by the operator in this manner. The line segments may be drawn either in the entire measuring region or only within the region-of-interest. However, it would be less troublesome for the operator to draw a line segment, representing the boundary, only within the region-of-interest.

Subsequently, using the user interface 208 again, the operator selects one of multiple areas that have been defined by the boundary being superimposed on the tomographic image on the display section 214. Then, the area selecting section 212 generates the location information of that area selected by the operator. The selected area location information thus generated is then output to the property value calculating section 207.

The ultrasonic diagnostic apparatus 102 operates just as the first preferred embodiment described above except that a boundary between tissues is defined manually by the operator within either the measuring region or the region-of-interest.

Figure 7:
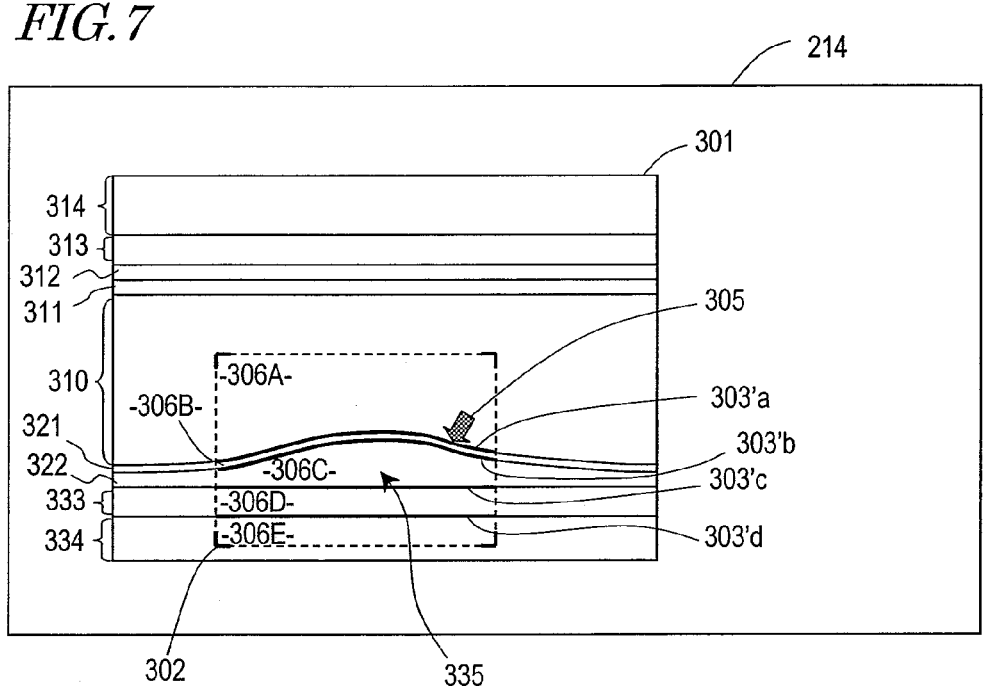
FIG. 7 illustrates an example of an image to be presented on the display section of the ultrasonic diagnostic apparatus shown in FIG. 6.

FIG. 7 illustrates how the operator have fixed boundaries 303'a, 303'b, 303'c and 303'd by drawing line segments between the respective tissues with the cursor 305 moved using the user interface 208.

Figure 8:
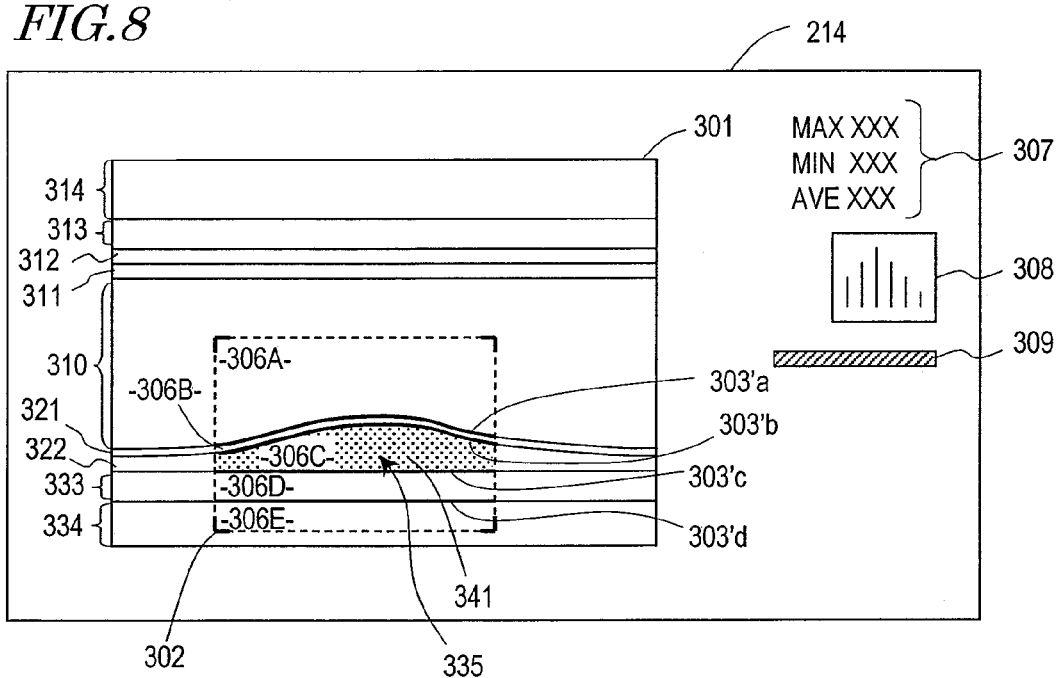
FIG. 8 illustrates another example of an image to be presented on the display section of the ultrasonic diagnostic apparatus shown in FIG. 6.
Figure 9:
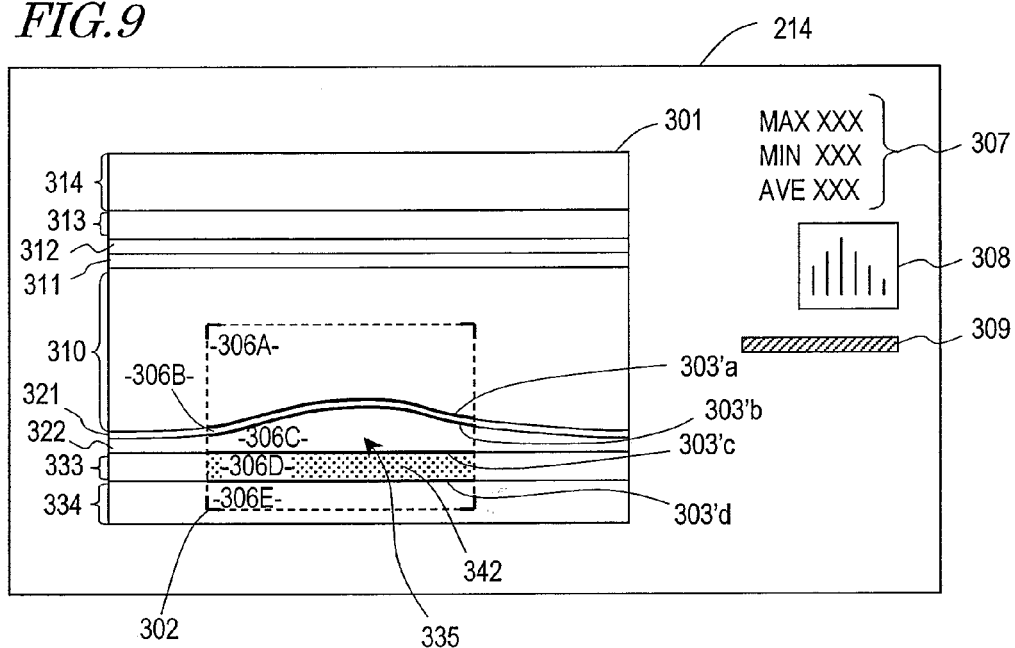
FIG. 9 illustrates still another example of an image to be presented on the display section of the ultrasonic diagnostic apparatus shown in FIG. 6.

In FIG. 7, if the operator has selected the area 306C interposed between the boundaries 303'b and 303'c, then a two-dimensional distribution image 341 of elastic moduli within the area 306C is superimposed on the tomographic image 301 as shown in FIG. 8. On the other hand, if the operator has selected the area 306D interposed between the boundaries 303'c and 303'd in FIG. 7, then a two-dimensional distribution image 342 of elastic moduli within the area 306D is superimposed on the tomographic image 301 as shown in FIG. 9.

Thus, according to this preferred embodiment, a boundary between tissues in a subject is drawn manually by the operator and one of the areas divided by the boundary is selected, thereby getting a two-dimensional distribution image of elastic moduli presented for any desired tissue. In particular, since the operator draws the boundary manually in this preferred embodiment, a target area where the elastic modulus needs to be calculated may be determined both arbitrarily and easily by collectively selecting a plurality of tissues as a single area and by getting the two-dimensional distribution image of elastic moduli presented in that selected area, for example. Also, even if the boundary between tissues has become locally indefinite on the tomographic image 301, the boundary can still be defined according to the operator's own judgment. That is why it is possible to avoid the unwanted situation where such an indefinite boundary prevents the operator from finding his or her target area and obtaining a two-dimensional distribution image of elastic moduli. Consequently, the distribution of elastic moduli can be known for every tissue within the measuring region and a more accurate pathological diagnosis can be made on the subject.

(Embodiment 3)

Figure 10:
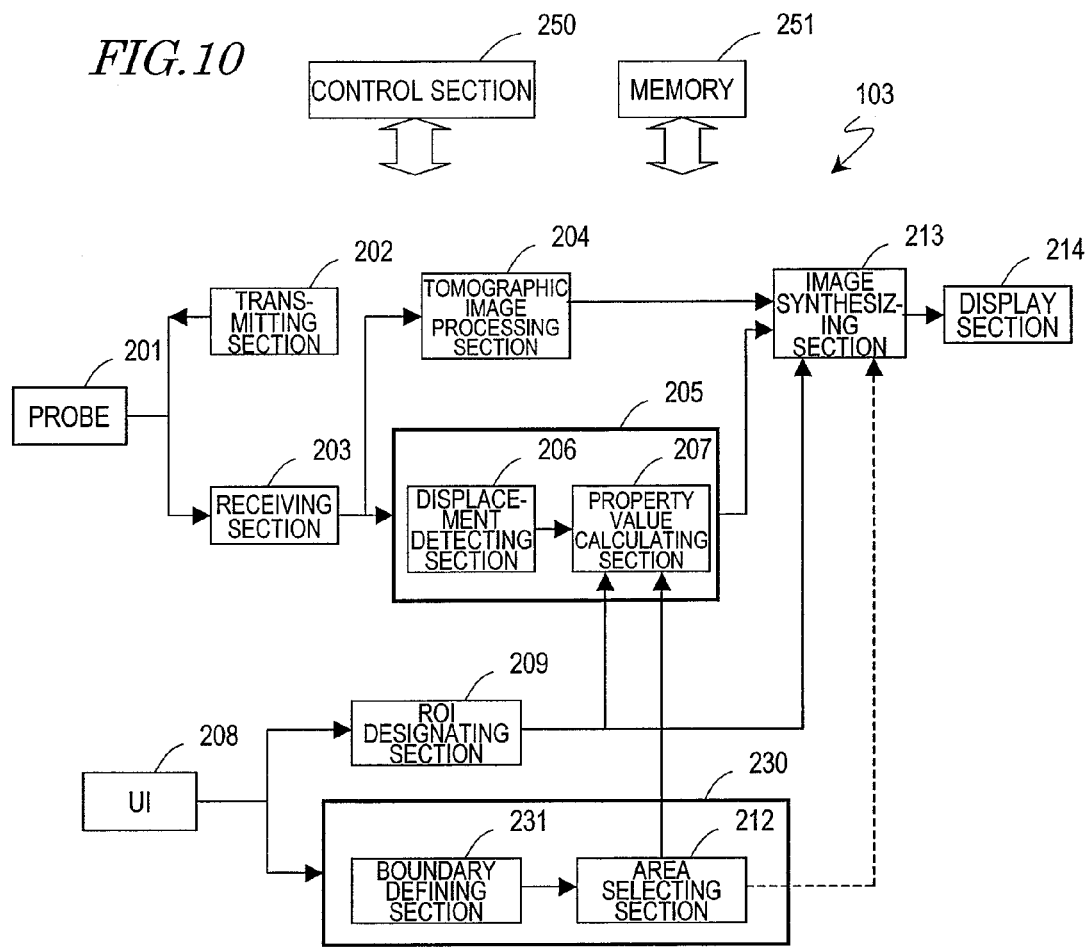
FIG. 10 is a block diagram illustrating a third preferred embodiment of an ultrasonic diagnostic apparatus according to the present invention.

Hereinafter, a third preferred embodiment of an ultrasonic diagnostic apparatus according to the present invention will be described. FIG. 10 is a block diagram showing a configuration for an ultrasonic diagnostic apparatus 103 as a third preferred embodiment of the present invention. Unlike the first preferred embodiment described above, the ultrasonic diagnostic apparatus 102 includes a memory 251 functioning as a storage section and a tissue-to-present determining section 230 including a boundary defining section 231.

While an ultrasonic wave is being transmitted or received to carry out measurements, the memory 251 stores information about an image signal representing the tomographic image, which has been provided by the tomographic image processing section 204, and information about the magnitude of displacement at each measuring point, which has been provided by the displacement detecting section 206, in association with the time or order of reception of the received signals. The memory 251 also stores the location information of the boundaries that have been defined by the boundary defining section 231.

In calculating an elastic modulus by reading the information that is stored in the memory section after the measuring process has ended or suspended (or frozen) (which is also called a "cine-mode"), the image information of the tomographic image and the information about the magnitude of displacement at each measuring point, which are stored in the memory 251, are read from the memory 251 and supplied to the image synthesizing section 213 and the property value calculating section 207, respectively, at the same time in accordance with a command given by the operator. In addition, the location information of the boundary is also read from the memory 251 and supplied to the boundary defining section 231.

While transmitting or receiving an ultrasonic wave and making a measurement, the boundary defining section 231 automatically detects the boundary between tissues based on the received signal as already described for the first preferred embodiment, thereby outputting its location information. Also, in calculating an elastic modulus by reading out the information stored, the operator can modify the boundary that has been read out from the memory 251 using the user interface 208. The modification includes deleting the boundary. If the boundary has been modified by the operator, the boundary defining section 231 obtains the location information of the modified boundary and updates the location information.

Then, based on the location information of the updated boundary, the operator selects a target area where the two-dimensional distribution of elastic moduli needs to be obtained as already described for the first preferred embodiment, thereby producing an image representing the two-dimensional distribution of elastic moduli in the selected area.

Figure 11:
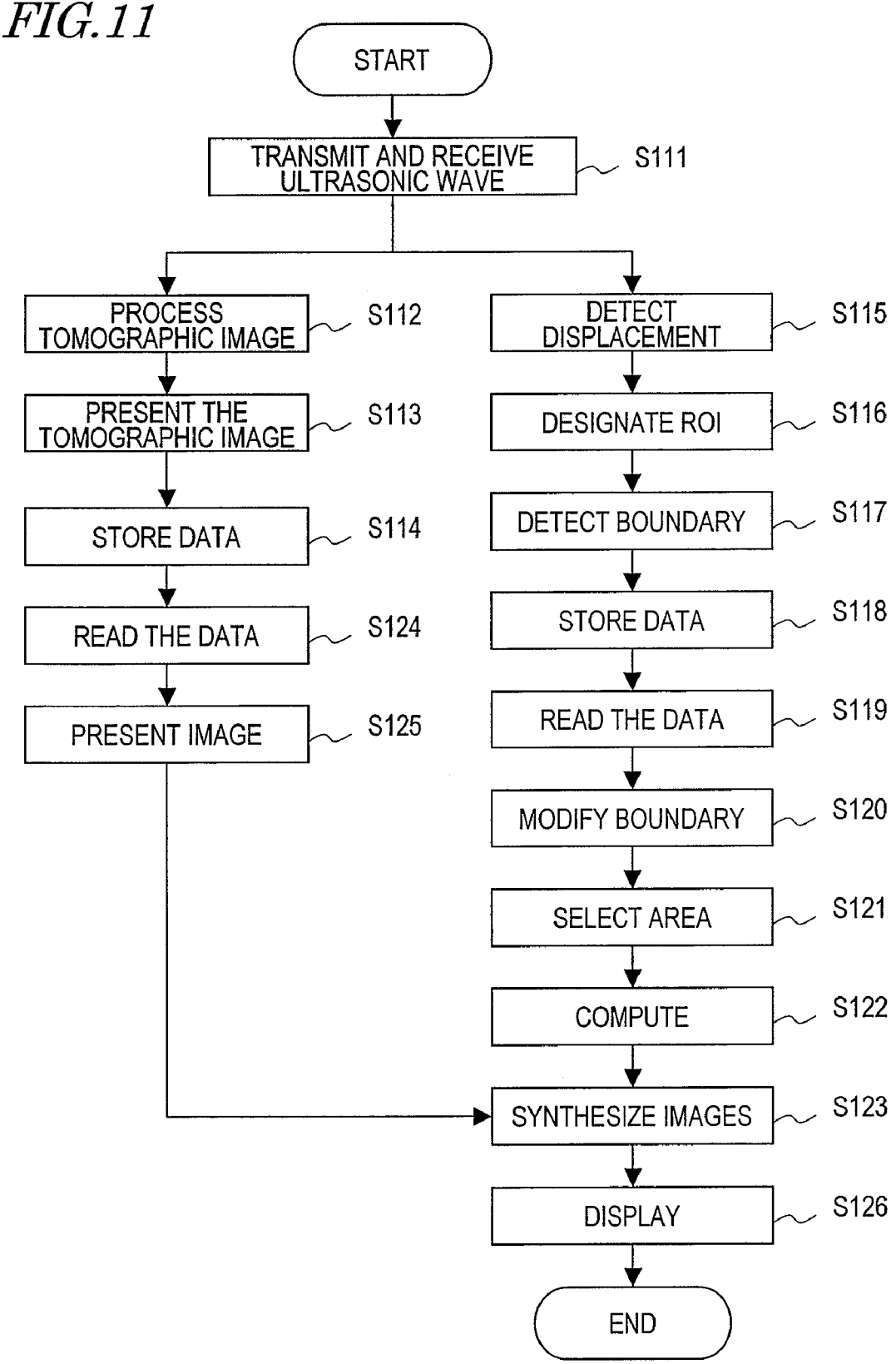
FIG. 11 is a flowchart showing how the ultrasonic diagnostic apparatus shown in FIG. 10 operates.
Figure 12:
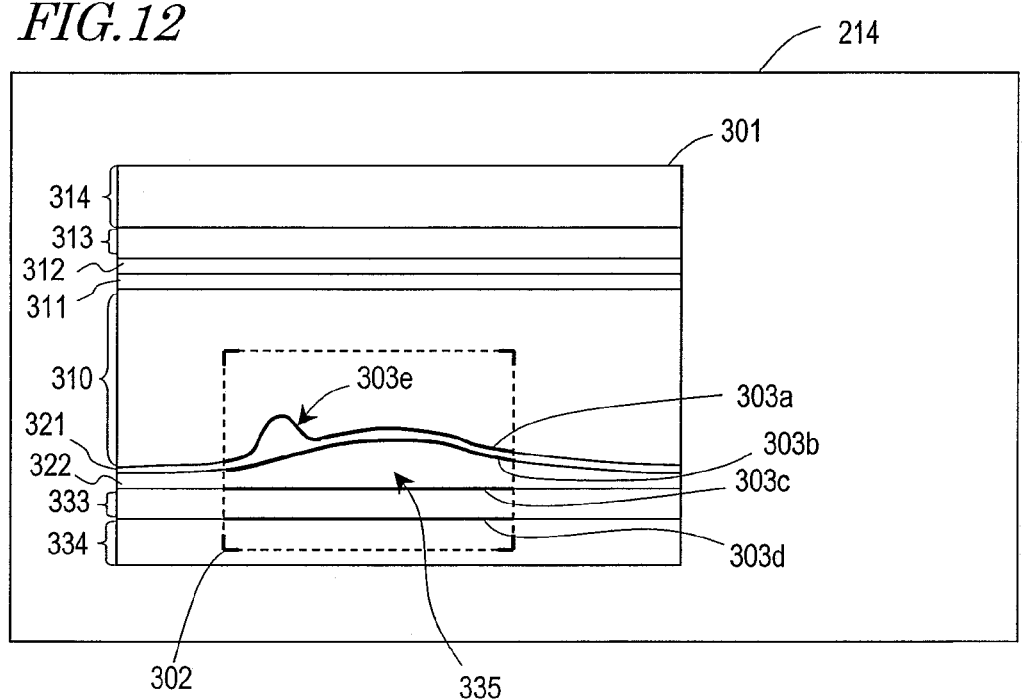
FIG. 12 illustrates an example of an image to be presented on the display section of the ultrasonic diagnostic apparatus shown in FIG. 10.
Figure 13:
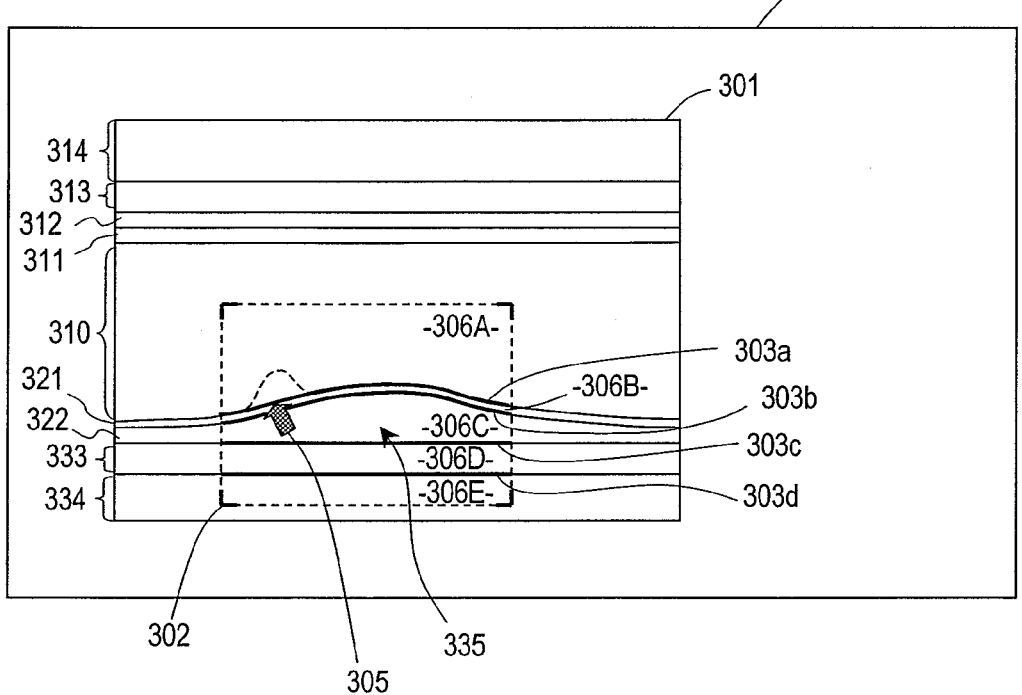
FIG. 13 illustrates another example of an image to be presented on the display section of the ultrasonic diagnostic apparatus shown in FIG. 10.
Figure 14:
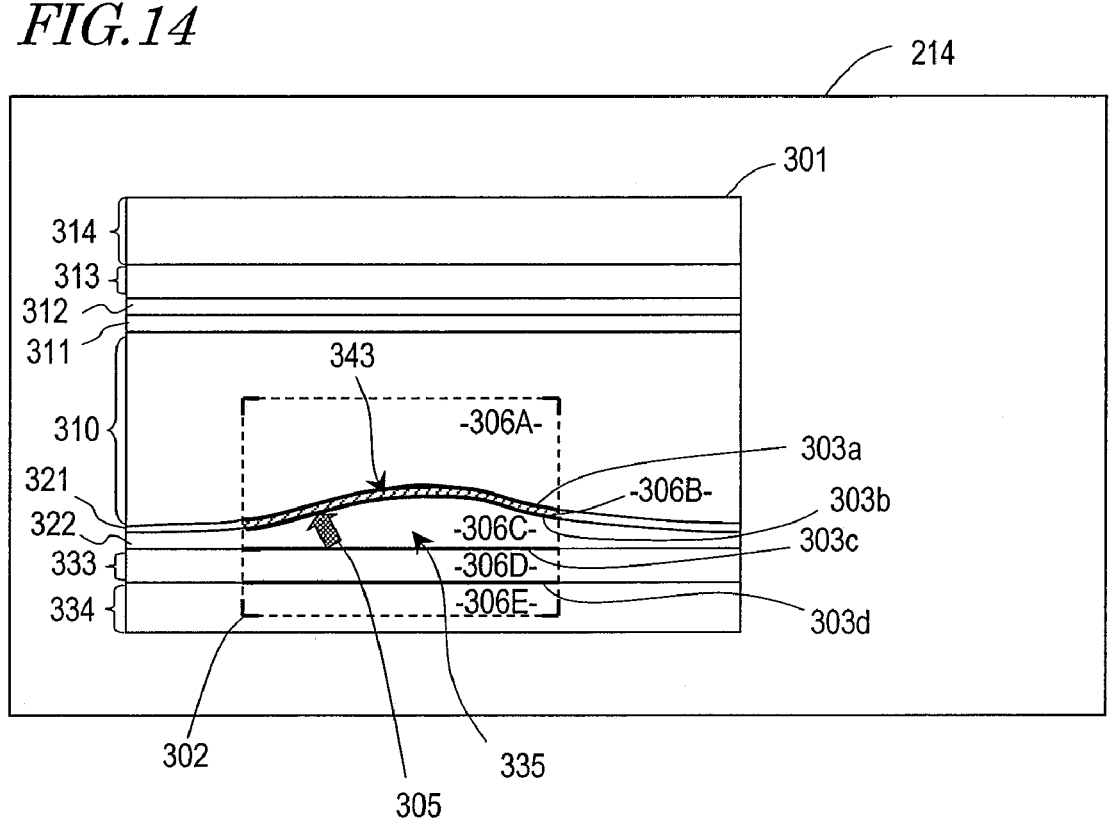
FIG. 14 illustrates still another example of an image to be presented on the display section of the ultrasonic diagnostic apparatus shown in FIG. 10.

Hereinafter, it will be described with reference to FIG. 10 and FIGS. 11 to 14 how the ultrasonic diagnostic apparatus 103 operates. FIG. 11 is a flowchart showing the procedure of operation of the ultrasonic diagnostic apparatus 103. FIGS. 12 to 14 illustrate exemplary images to be presented on the display section 214.

First, the transmitting section 202 drives the probe 201, thereby sending out an ultrasonic wave toward a subject including his or her arterial vascular wall. Then, a reflected wave, produced by getting the ultrasonic wave reflected by the subject, is received at the receiving section 203 through the probe 201, thereby generating a received signal in Step S111.

The tomographic image processing section 204 receives the received signal and transforms the amplitude of the received signal into luminance information, thereby generating an image signal representing a tomographic image (in Step S112). Then, the image signal is output to the display section 214 by way of the image synthesizing section 213, and the tomographic image is presented on the display section (in Step S113).

As shown in FIG. 14, a tomographic image 301 is presented on the screen of the display section 214. The tomographic image 301 includes the intima 311, media 312 and adventitia 313 of a vascular anterior wall, the intima 321, media 322 and adventitia 323 of a vascular posterior wall, a vascular lumen 310, and extravascular tissues 314 and 334.

While the tomographic image is being generated, the displacement detecting section 206 of the computing section 205 analyzes the received signal, thereby calculating the magnitudes of displacements of respective measuring points within the measuring region of the subject (in Step S115).

The operator defines a region-of-interest 302 using a user interface 208 such as a mouse. In the example illustrated in FIG. 12, the region-of-interest 302 is defined by the operator so as to include an atheroma 335 that is observed on the vascular posterior wall. In accordance with the signal that has been entered through the user interface 208, the ROI designating section 209 determines the location information of the region-of-interest 302 within the measuring region (in Step S116). Optionally, the region-of-interest may also be defined after a target area where an attribute property value needs to be calculated has been selected.

The measuring process is carried out in such a state for a predetermined period of time, thereby obtaining measuring data. The image information to be generated sequentially and the magnitudes of displacements of the respective measuring points are stored in the memory 21 in associated with the reception times (in Steps S114 and S118). The location information of the boundary that has been detected automatically (in Step S117) is also stored.

When the measuring process ends, the image information, the magnitudes of displacements of the respective measuring points, and the location information of the boundary, which have been stored in the memory 251, are read out (in Step S119 or S124). And the image information and the boundary are presented on the display section 214 (in Step S125 or S126).

If necessary, the operator modifies the automatically detected boundary on the tomographic image 301 being presented on the display section 214. In FIG. 12, a portion 303e of the automatically detected boundary 303a expands toward the vascular lumen 310. If the operator has determined, based on the tomographic image 301, that the location of that portion 303e of the boundary is a detection error, then he or she modifies the location of that portion 303e of the boundary by moving the cursor 305 as shown in FIG. 13. Once the boundary has been modified, the boundary defining section 231 updates the location information of that boundary modified (in Step S120).

Then, the operator chooses one of the areas 306A, 306B, 306C, 306D and 306E, which have been defined by the modified boundary 303a and the other boundaries 303b through 303d, as a target area where the attribute property value needs to be calculated. By moving the cursor 305 with the user interface 208 as shown in FIG. 13, for example, the operator designates one particular area. In accordance with the signal supplied from the user interface 208, the area selecting section 212 generates the location information of the selected area that has been designated by the operator and outputs the information to the property value calculating section 207 and the image synthesizing section 213 (in Step S121).

Based on the magnitudes of displacement at the respective measuring points that have been provided by the displacement detecting section 206 and the location information of the selected area that has been provided by the tissue-to-present determining section 210, the property value calculating section 207 calculates the elastic modulus between the measuring points within the selected area. The property value calculating section 207 also obtains the maximum, minimum and average values and frequency distribution of the elastic moduli within the selected area (in Step S122).

The image synthesizing section 213 generates a two-dimensional distribution image based on the elastic moduli that have been calculated by the property value calculating section 207 and synthesizes the distribution image and the tomographic image together. The image synthesizing section 213 also generates numerical values representing the maximum, minimum and average values and further generates a histogram of the elastic moduli in Step S123. The image thus generated is presented on the display section 214 (in Step S126).

After that, the selected area where the attribute property value needs to be obtained may be modified or changed if necessary. In that case, the same series of processing steps that starts with Step S121 should be carried out all over again.

In FIG. 13, if the operator has selected the area 306B interposed between the boundaries 303a and 303b, then a two-dimensional distribution image 343 of elastic moduli within the area 306B is superimposed on the tomographic image 301 as shown in FIG. 14. The area 306B is a portion of the designated region-of-interest 302 that represents the intima of the vascular posterior wall. Since the operator has modified the boundary 303a, the elastic modulus of only the intima portion is displayed properly. Although not shown in FIG. 14, the maximum, minimum and average values of elastic moduli in the selected area and histograms of the elastic moduli may also be displayed as in the first and second preferred embodiments described above.

As described above, according to this preferred embodiment, when the elastic modulus is calculated by reading information from the memory in the cine-mode after the boundary between tissues in the subject has been detected automatically, the operator can modify the automatically detected boundary. Thus, the operator can save the trouble of drawing the boundary by him- or herself and can modify the boundary manually if necessary. As a result, the target tissue, of which the elastic modulus needs to be calculated, can be determined more easily and more accurately, and the distribution of elastic moduli can be known for every tissue within the measuring region. Consequently, a pathological diagnosis can be made on the subject more accurately.

In the preferred embodiment described above, the boundary defining section 231 is designed so as to automatically detect the boundary between tissues first, read the data from the memory, and then allow the operator to modify the detected boundary if necessary. Likewise, the boundary defining section of the first preferred embodiment described above may also be designed so as to automatically detect the boundary and then allow the operator to modify the boundary if necessary. More specifically, the boundary defining section 211 may automatically generate the location information of at least one boundary based on the received signal. Then, the operator may modify and update the location information of the at least one boundary, which has been generated by the boundary defining section 211, based on the location specified by the operator on the tomographic image being presented on the display section 214. As a result, the boundary can be defined more accurately and the burden on the operator can be lightened, too.

INDUSTRIAL APPLICABILITY

The present invention can be used effectively in an ultrasonic diagnostic apparatus for measuring an attribute property value of a blood vessel.

The invention claimed is:

1. An ultrasonic diagnostic apparatus comprising:
a transmitting section configured to drive an ultrasonic probe that sends out an ultrasonic wave toward a measuring region of a subject, the region including an arterial vascular wall;
a receiving section configured to receive a reflected wave, produced by getting the ultrasonic wave reflected from the subject, at the ultrasonic probe, thereby generating a received signal;
an image processing section configured to generate a tomographic image of the measuring region of the subject based on the received signal;
a display section configured to present the tomographic image;
a displacement detecting section configured to calculate a magnitude of displacement of each of a plurality of measuring points in the measuring region on the vascular wall by analyzing the received signal;
a tissue-to-present determining section, configured to define at least one boundary between multiple tissues included in the measuring region on the vascular wall based on the tomographic image displayed by the display section and configured to receive a selection of a desired one from at least two areas that have been divided by the at least one boundary defined; and
a property value calculating section configured to calculate a property value of the desired one area based on the magnitude of displacement of each said measuring point included in the desired one area selected by the tissue-to-present determining section,
wherein the display section superimposes and presents on the tomographic image a distribution of property values of the measuring points included in the desired one area that has been calculated by the property value calculating section as a two-dimensional image;
wherein the property value is at least one of an elastic modulus, magnitude of strain, and coefficient of viscosity.

2. The ultrasonic diagnostic apparatus of claim 1, wherein the tissue-to-present determining section includes: a boundary defining section for defining at least one boundary between the multiple tissues included in the vascular wall; and an area selecting section for selecting one from the at least two areas that have been divided by the boundary defined, and
wherein the area selecting section generates location information of the one area in accordance with an operator's command and outputs the location information to the property value calculating section.

3. The ultrasonic diagnostic apparatus of claim 2, wherein the boundary defining section generates the location information of the at least one boundary based on a location that has been specified by the operator on the tomographic image presented on the display section.

4. The ultrasonic diagnostic apparatus of claim 2, wherein the boundary defining section automatically generates the location information of the at least one boundary based on the received signal.

5. The ultrasonic diagnostic apparatus of claim 4, further comprising a storage section that stores not only the location information of the at least one boundary but also information about the tomographic image and information about the magnitudes of displacement of the respective measuring points in association with points in time when, or the order in which, the received signals arrived.

6. The ultrasonic diagnostic apparatus of claim 5, wherein the information about the tomographic image is read from the storage section to present the tomographic image on the display section, and the boundary defining section reads the location information of the at least one boundary between the tissues from the storage section, and
wherein the boundary defining section updates the location of the at least one boundary based on the location that has been specified by the operator on the tomographic image presented on the display section.

7. The ultrasonic diagnostic apparatus of claim 2, wherein the boundary defining section automatically generates the location information of the at least one boundary based on the received signal, and updates the location information of the at least one boundary generated based on the location that has been specified by the operator on the tomographic image presented on the display section.

8. The ultrasonic diagnostic apparatus of claim 1, further comprising a region-of-interest designating section for allowing the operator to designate a region of interest within the measuring region based on the tomographic image presented on the display section, and
wherein the property value calculating section calculates a property value of the subject based on the magnitude of displacement of a measuring point inside the region of interest.

9. The ultrasonic diagnostic apparatus of claim 8, wherein the property value calculating section further calculates at least one of the average, maximum value, minimum value and variance of elastic moduli within the region of interest.

10. The ultrasonic diagnostic apparatus of claim 8, wherein the property value calculating section further figures out a distribution of elastic moduli within the region of interest and presents the distribution of elastic moduli as a histogram on the display section.

11. The ultrasonic diagnostic apparatus of claim 1, wherein the vascular wall includes an intima, a media and an adventitia and wherein the at least one boundary is at least one of a boundary between the intima and a vascular lumen, a boundary between the intima and the adventitia, and a boundary between the adventitia and an extravascular tissue.

12. A method for controlling an ultrasonic diagnostic apparatus using a control section of the apparatus, the method comprising the steps of:
(A) driving an ultrasonic probe and sending out an ultrasonic wave;
(B) receiving a reflected wave from a subject, including an arterial vascular wall, at the ultrasonic probe, thereby generating a received signal, generating a tomographic image of the measuring region of the subject based on the received signal, and presenting in a display section the tomographic image;
(C) calculating a magnitude of displacement of each of a plurality of measuring points in a measuring region on the vascular wall by analyzing the received signal;
(D) defining at least one boundary between multiple tissues included in the measuring region on the vascular wall based on the tomographic image displayed by the display section and selecting a desired one from at least two areas that have been divided by the boundary defined;

(E) calculating a property value of the desired one area based on the magnitude of displacement of each said measuring point included in the selected desired one area, wherein the property value is at least one of an leastic modulus, magnitude of strain, and coefficient of viscosity; and (F) superposing and presenting on the tomographic image the property value of the desired one area as a two-dimensional image.

13. The method of claim 12, wherein the step (D) includes the steps of:
   (D1) defining the at least one boundary between the multiple tissues included in the vascular wall; and
   (D2) selecting the desired one from the at least two areas that have been divided by the boundary defined, and
   wherein the step (D2) includes generating location information of the one area in accordance with an operator's command.

14. The method of claim 13, wherein the step (D1) includes generating location information of the at least one boundary based on a location that has been specified by the operator on the tomographic image.

15. The method of claim 13, wherein the step (D1) includes automatically generating the location information of the at least one boundary based on the received signal.

16. The method of claim 15, further comprising, between the steps (D) and (E), the step (I) of storing, in the storage section, not only the location information of the at least one boundary but also information about the tomographic image and information about the magnitudes of displacement of the respective measuring points in association with points in time when, or the order in which, the received signals arrived.

17. The method of claim 16, further comprising, between the steps (D) and (E), the step (J) of reading the information about the tomographic image from the storage section to present the tomographic image on the display section, and making the boundary defining section retrieve the location information of the at least one boundary between the tissues from the storage section, and
   the step (K) of updating the location information of the at least one boundary by allowing the operator to modify the location of the at least one boundary on the tomographic image.

* * * * *